United States Patent [19]

Wampler

[11] Patent Number: 4,767,591
[45] Date of Patent: Aug. 30, 1988

[54] RESISTANCE PROBE FOR ENERGETIC PARTICLE DOSIMETRY

[75] Inventor: William R. Wampler, Albuquerque, N. Mex.

[73] Assignee: The United States of America as represented by the Department of Energy, Washington, D.C.

[21] Appl. No.: 468,930

[22] Filed: Feb. 23, 1983

[51] Int. Cl.⁴ .............................................. G21B 1/00
[52] U.S. Cl. ....................................... 376/143; 324/64
[58] Field of Search ........................... 376/143; 324/64

[56] References Cited

U.S. PATENT DOCUMENTS

| | | |
|---|---|---|
| 2,564,626 | 8/1951 | MacMahon et al. |
| 3,045,198 | 7/1962 | Dolan et al. |
| 3,416,078 | 12/1968 | Boncuk et al. .......................... 324/64 |
| 4,218,650 | 8/1980 | Matzen .................................. 324/64 |

OTHER PUBLICATIONS

*Journal of Nuclear Materials*, vol. 102, Jun. 1981, "Saturation of Deuterium Retention in Carbon a New Calibration for Plasma Edge Probes", Wampler et al.

"A Resistance Probe for Energetic Particle Dosimetry with Applications for Plasma Edge Studies", Aug. 1982, Wampler.

*Primary Examiner*—Deborah L. Kyle
*Assistant Examiner*—Richard L. Klein
*Attorney, Agent, or Firm*—George H. Libman; James H. Chafin; Judson R. Hightower

[57] ABSTRACT

A probe for determining the energy and flux of particles in a plasma comprises a carbon film adapted to be exposed to the plasma, the film havinmg an electrical resistance which is related to the number of particles impacting the film, contacts for passing an electrical current through the film, and contacts for determining the electrical resistance of the film. An improved method for determining the energy or flux of particles in a plasma is also disclosed.

15 Claims, 3 Drawing Sheets

4,767,591

RESISTANCE PROBE FOR ENERGETIC PARTICLE DOSIMETRY

The U.S. Government has rights in this invention pursuant to Contract No. DE-AC04-76DP00789 between the U.S. Department of Energy and Western Electric Company.

BACKGROUND OF THE INVENTION

It is often desirable to determine the energies and doses of particles incident on materials exposed to a plasma. For example, the successful design of a fusion reactor based on magnetic confinement requires an understanding of conditions at the boundary region between the magnetically confined plasma and the reactor wall. The particles of interest are usually hydrogen or deuterium with energies and fluxes typically in the range of 10 to 1000 eV and $10^{12}$ to $10^{18}$ particles per square centimeter per second, respectively. In the past, such studies have generally relied on ion beam analysis or sputter profiling measurements to determine the dose and energy of the particles retained in probe samples exposed to the plasma edge. However, such techniques require specialized facilities and considerable effort to perform the analysis. Additionally, ion beam analysis or sputter profiling cannot provide the desired information during exposure of the probe.

A technique for measuring neutron doses is disclosed in U.S. Pat. No. 2,564,626 to MacMahon et al. This device includes a boron, lithium, aluminum or lead element which is exposed to a neutron beam. Changes in the resistance of the element resulting from nuclear transmutation indicate the neutron dose. However, this device cannot be used to detect energetic ions.

Accordingly, it is an object of the present invention to overcome the disadvantages associated with devices and methods known in the prior art.

An object of the invention is to provide a simplified means and method for determining the energy and integrated dose of energetic ions and neutral particles in a plasma.

It is an object of the invention to provide means for obtaining desired information regarding a plasma continuously during exposure of a probe to the plasma.

SUMMARY OF THE INVENTION

The invention comprises improved means and method for determining the energy and flux of particles in a plasma which do not suffer from the drawbacks associated with the prior art devices and techniques. The inventive means and method are capable of determining energy and flux of both ions and neutral particles, and can provide desired information continuously during exposure of a probe to the plasma. Additionally, a probe in accordance with the invention is capable of detecting low energy particles at low doses, and represents a substantial improvement over the prior art.

The invention is based upon an observed change in the electrical resistance of a thin carbon film upon bombardment of the film by particles. A probe in accordance with the invention comprises a carbon film which may be evaporated onto a substrate. Particles bombarding the film become implanted therein, increasing the resistivity of the film. Means are provided for passing an electrical current through the film, and for measuring the resulting voltage across the film. From the measured voltage, the resistance, and thus the number of particles implanted in the film, can be determined.

A probe in accordance with the invention may be shielded from low energy particles by applying an insulating layer thereto or by imposing a positive bias voltage on the carbon film. Imposing the positive bias voltage may also serve to separate charged particles from neutral particles.

In use, a probe in accordance with the invention is exposed to a plasma edge, whereby the carbon film is exposed to the particles of the plasma. The desired information, from which particle energy and flux may be determined, may be continuously obtained during exposure of the probe to the plasma by monitoring the electrical resistance of the probe.

BRIEF DESCRIPTION OF THE DRAWINGS

The objects and advantages of the present invention will be best understood in light of the following detailed description, taken together with the accompanying drawings in which.

DETAILED DESCRIPTION OF A PREFERRED EMBODIMENT

Figure 1:
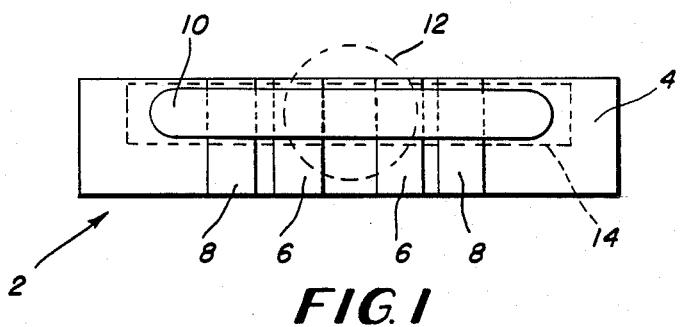
FIG. 1 illustrates an exemplary embodiment of a probe in accordance with the invention.

FIG. 1 illustrates a probe in accordance with the present invention, designated generally be reference numeral 2. Probe 2 comprises a substrate 4 which may be, for example, glass or silica. A pair of inner metal contacts 6 are supported by substrate 4. Contacts 6 preferably comprise metal films deposited onto the substrate. A pair of outer metal contacts 8 are also provided. Contacts 8 may likewise comprise metal films deposited on substrate 4.

A carbon film 10 is deposited on substrate 4 over and in intimate electrical contact with metal contacts 6 and 8. Carbon film 10 includes an implant area 12 which is exposed to a plasma when the probe is used in plasma analysis, as described in greater detail hereinafter. Thus, particles of the plasma will bombard carbon film 10 within area 12. An inner contact 6 and an outer contact 8 are positioned on each side of implant area 12.

Probe 2 may optionally comprise an insulating layer 14 of silicon or the like, for a purpose to be described in greater detail hereinafter.

In preparing the probe 2, it is important to anneal the films at about 700° C. for approximately one hour in a vacuum to reduce the initial resistance of the films. Upon exposure of carbon film 10 to a plasma, the resistance thereof will vary in accordance with the number of particles implanted in the film.

In use, probe 2 is exposed to the edge of a plasma in such manner that implant area 12 is bombarded by particles of the plasma. An electrical current is applied to carbon film 10 across outer contacts 8. Voltage across implant area 12 is measured by means of inner contacts 6. From the known current and measured voltage, the electrical resistance of the implant area may be calculated. Use of four contacts 6, 8 avoids undesired effects of contact resistance.

Measurements were made of the changes in electrical resistance of carbon films caused by implantation of hydrogen, deuterium and carbon at various energies. The probes were prepared by evaporation of metal contacts and carbon films onto fused silica substrates, as described above. Two sets of probes were prepared. The first set had a carbon film thickness of 49±5 nm with gold contacts. The second set had a carbon film thickness of 92±9 nm with contacts comprising 50 nm Ni on 10 nm of Cr. The thinner (49 nm) carbon film was deposited at 0.1 nm/s in a $5 \times 10^{-7}$ torr vacuum and the thicker (92 nm) film at 0.17 nm/s in a $2 \times 10^{-7}$ torr vacuum. A density of 1.8 g/cm$^3$ for the carbon was assumed.

The resistance of the probes as deposited was 5 kΩ for the thin carbon film and 1 kΩ for the thicker film. Annealing in a vacuum at 700° C. for one hour lowered the resistance to 420±40 Ω for the thin film and 180±20 Ω for the thick film giving a resistivity after annealing of 1.75±0.2 mΩcm for each film. The film resistance seemed to be unaffected by exposure to air.

A series of experiments was conducted in which the resistance of the annealed carbon films was measured as a function of incident particle fluence as determined by current integration. The resolution of the resistance measurement (1 in $10^5$) determined the lowest fluence at which measurements could be made. However, use of a bridge-type of measurement circuit to provide an offset should allow measurements to be made at much lower fluences.

The temperature coefficient of resistance was measured on a carbon film probe after the initial annealing treatment but before exposure to a plasma. The temperature coefficient was found to be $-3.75 \times 10^{-4}$/°C. Temperature changes during the experimental exposures of the respective probes, as monitored by a thermocouple, were noted to be much less than 1° C., resulting in resistance changes much less than those caused by particle implantation.

Figure 2:
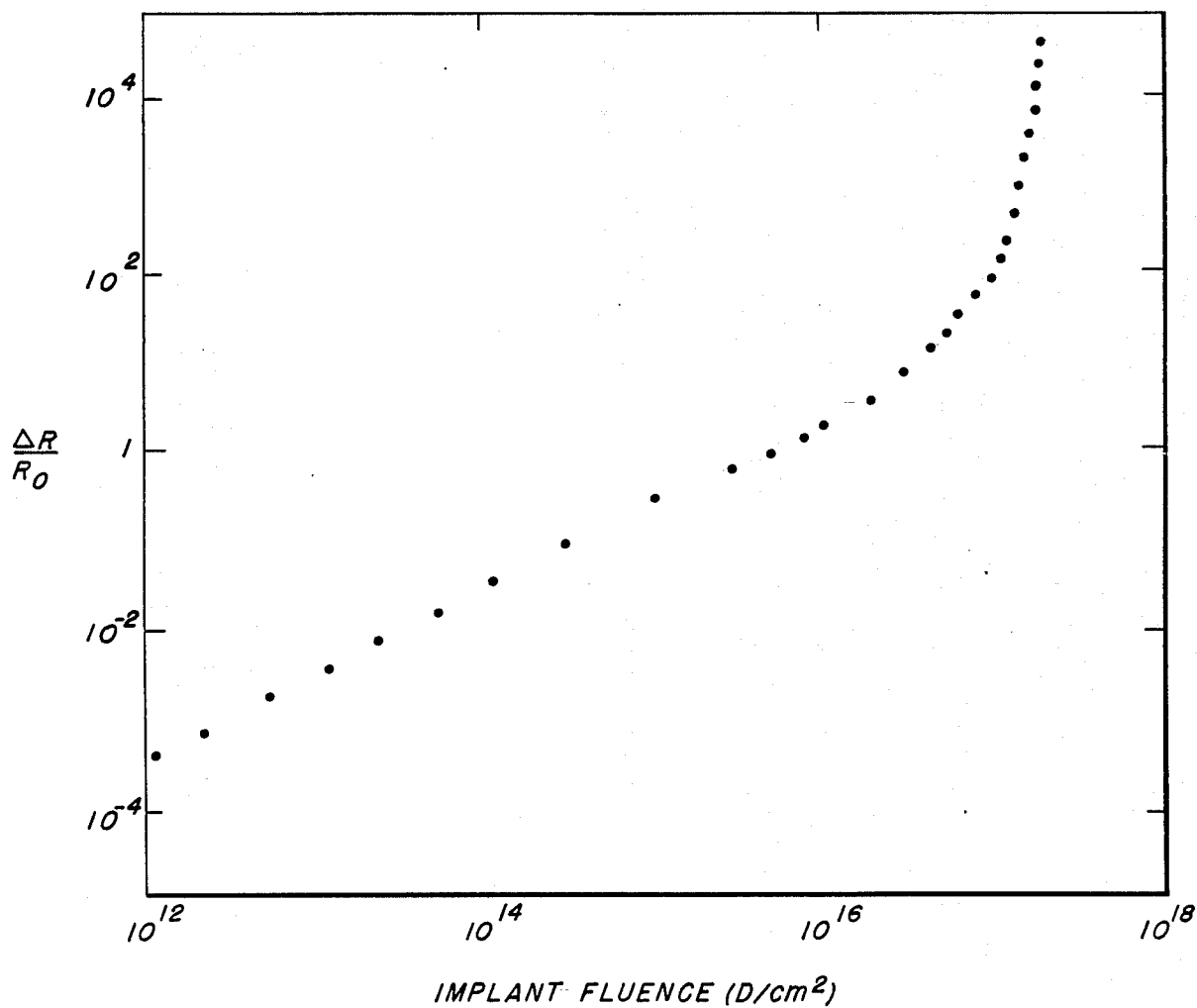
FIG. 2 is a graphical illustration of the fractional change in the resistance of a carbon film caused by implantation with deuterium.

FIG. 2 is a graph showing the fractional change in resistance of a 92 nm thick carbon film resulting from implantation with deuterium at 3 keV. At this energy, the entire thickness of the film is implanted. The resistance increases proportionally with deuterium fluence up to a fluence of approximately $10^{16}$ D/cm$^2$. At approximately $10^{17}$ D/cm$^2$ the resistance begins to increase much more rapidly with D fluence. This is the fluence where the deuterium retention in the carbon saturates. It was also observed that the implantation decreased the optical density of the carbon film.

Figure 3:
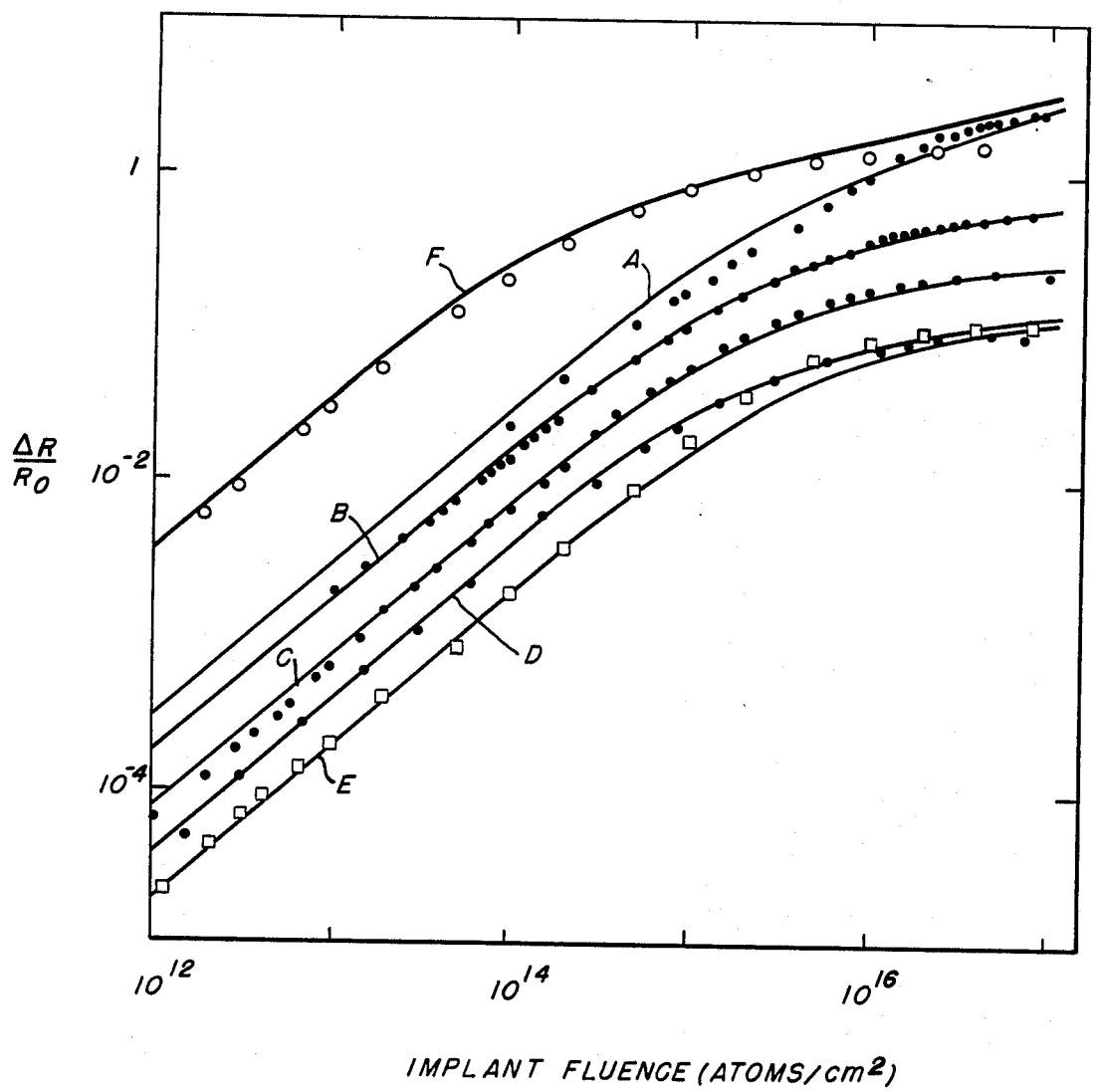
FIG. 3 graphically illustrates the relative change in the resistance of carbon films caused by implantation of various particles.

FIG. 3 graphically illustrates the relative changes in the resistance of carbon films when the range (depth) of the implanted particles is less than the thickness of the film. Data sets A, B and C (points corresponding generally to curves A, B and C, respectively) show the results for probes having a carbon film thickness of 45 nm implanted with deuterium at 500, 250 and 125 eV, respectively. The solid line curves were calculated using a model to be described in greater detail hereinafter. At fluences below approximately $10^{15}$ D/cm$^2$ the change in resistance is proportional to D fluence as discussed above. A fluences of about $10^{17}$ D/cm$^2$ the resistance is no longer increasing with D fluence. The reason for this saturation effect is that the conductivity of the implanted carbon has become negligible compared to the conductivity of the underlying unimplanted carbon. Further implantation has little effect on the net resistance of the carbon film which becomes dependent primarily upon the conductivity of the unimplanted portion of the film. In this high fluence limit the fractional change in resistance can be expressed as:

$$\frac{\Delta R}{R_o} = \frac{\delta}{\tau - \delta} \qquad (1)$$

wherein $\delta$ is the thickness of the implanted layer and $\tau$ is the carbon film thickness. Table 1 gives the values of $\delta$ obtained from the saturation values of $\Delta R/R_o$ (from FIG. 3 at a fluence of $10^{17}$ atoms/cm$_2$) using Equation 1. For data sets A, B and C, $\delta$ varies nearly linearly with the incident particle energy.

Data set D was measured for the same implant conditions as data set C but with a thicker (92 nm) carbon film. Data set E in FIG. 3 was measured under the same conditions as set D except that hydrogen was implanted instead of deuterium. The resistance changes at saturation (and therefore $\delta$) for the hydrogen and deuterium implants are nearly equal as would be expected from the fact that the ranges of these particles are almost the same. However, at low fluence, the resistance change for the hydrogen implant is less than that for the deuterium implant at the same energy and fluence by a factor of 2.

Data set F in FIG. 3 was measured for a probe having a carbon film thickness of 49 nm implanted with carbon ions at 3 keV. The fact that the high fluence saturation level in the resistance change for the carbon implant is slightly below the level for the 500 eV deuterium implant is consistent with the range of these particles (see Table 1).

TABLE 1

| Sample* | Implanted Atoms | Energy (eV) | Carbon Thickness (nm) | δ (nm) | R (nm) | σ (nm) | ε (0 eV) | ε (5 eV) | ε (25 eV) |
|---|---|---|---|---|---|---|---|---|---|
| A | D | 500 | 49 | 35 | 5.6 | 7.5 | 0.53 | 0.40 | 0.23 |
| B | D | 250 | 49 | 18 | 2.5 | 3.8 | 0.62 | 0.44 | 0.18 |
| C | D | 125 | 49 | 10 | 0.9 | 2.2 | 0.64 | 0.39 | 0.098 |
| D | D | 125 | 92 | 8.0 | 0.9 | 2.2 | 0.64 | 0.39 | 0.098 |
| E | H | 125 | 92 | 8.7 | 0.7 | 2.3 | 0.43 | 0.19 | 0.0095 |
| F | C | 3000 | 49 | 31 | 3.9 | 6.4 | 0.83 | 0.81 | 0.74 |

*Sample Designations refer to the data of FIG. 3.

The increase in resistance caused by the carbon implant indicates that the cause of the resistance increase is lattice damage. It will be seen below that the dependence of the resistance change on the energy and mass of the incident particles is consistent with this.

The TRIM Monte Carlo particle transport code, as described in Biersack et al, Nucl. Inst. and Methods, Volume 174, P. 257 (1980), was used to calculate the particle and damage deposition profiles for hydrogen, deuterium and carbon projectiles onto a carbon target.

The depth profiles of the energy into atomic displacements obtained from these calculations could be closely represented by a Gaussian distribution:

$$\Gamma(x) = \frac{E\epsilon}{\sigma\sqrt{2\pi}} \exp\frac{-(x-R)^2}{2\sigma^2}, \quad (2)$$

where E is the incident particle energy and $\epsilon$ is the fractional portion of E into atomic collisions which exceeds the damage threshold energy. The values of $\epsilon$, the centroid R and standard deviation $\sigma$ of the distribution are given in Table 1 for a damage threshold of 5 eV. For comparison, the values of $\epsilon$ for damage thresholds of 0 eV and 25 eV are also provided. Measurements of changes in electrical resistance of carbon films during electron irradiation indicate a displacement threshold energy of 25 eV.

Since the resistance change is caused by lattice damage, it is reasonable to expect that the resistivity change should be proportional to the energy transformed into damage. If we define an effective local resistivity $\rho(x)$ at depth x and assume that this increases linearly with the amount of energy resulting in local damage, then:

$$\rho(x) = \rho_o + \alpha\phi\Gamma(x) \quad (3)$$

where $\rho_o$ is the resistivity of the unimplanted material, $\phi$ is the particle fluence and $\alpha$ is a coefficient which gives the resistivity change per unit damage. If we then assume that the resistance of the film can be expressed as an integral of the contributions from each depth increment, the relative resistance change is:

$$\frac{\Delta R}{R_o} = \left[\int_o^T \frac{\frac{dx}{T}}{1 + \frac{\alpha}{\rho_o}\phi\Gamma(x)}\right]^{-1} - 1 \quad (4)$$

The solid line curves shown in FIG. 3 were calculated using Equation 4 with a single value of the coefficient $\alpha = 1.3 \times 10^{-26} \Omega cm(eV/cm^3)^{-1}$ which resulted in a reasonably good fit for all of the data. The damage profiles used for these calculations were obtained from the TRIM code. However, it was found that a correct fit to the saturation levels requires that the actual damage profiles are broader by a factor of 1.4 than the calculated ones. Therefore, use of values for $\sigma$ in the calculations 1.4 times larger than the values in Table 1 obtained from the TRIM code is indicated. A further point to note is that, in the low fluence limit where $\alpha\phi\Gamma(x)/\rho_o \ll 1$, Equation 4 can be approximated by:

$$\frac{\Delta R}{R_o} \simeq \frac{\alpha\phi}{\rho_o T} \int_o^T \Gamma(x)dx = \frac{\alpha\phi\epsilon E}{\rho_o T} \quad (5)$$

which shows how the resistance depends on the various parameters in the low fluence region.

The solid line curves in FIG. 3 were calculated using values of $\epsilon$ from the TRIM calculations using a damage threshold energy of 5 eV. The values of $\epsilon$ for threshold energies of 0 or 25 eV (Table 1) would give worse fits to the data. This is evidenced by a comparison of the resistance change for the hydrogen and deuterium implants at 125 eV (curves D and E in FIG. 3).

The resistance change caused by particle bombardment, as described herein, can be advantageously used for plasma edge studies, as discussed above. A significant advantage offered by the presently disclosed device and method is that the effect of exposure of the carbon film to the plasma can be continuously monitored during the exposure. It may even be possible to obtain time resolved measurements during a single discharge.

In earlier studies, the fact that more energetic particles penetrated deeper into a film has been used to determine the energy of the incident particles. A resistance probe in accordance with the invention could be used in a similar fashion by measuring the resistance change as a function of exposure time or number of discharges. From the saturation level of $\Delta R/R_o$ at high fluence, the particle energy can be determined. Once the particle energy is known, the flux can also be deduced from the slope of $\Delta R/R_o$ versus $\phi$ at low fluence using Equation 5.

An alternative way to determine the particle energy for ions would be to measure how the resistance change caused by the incident ions varies with positive bias potential applied to the probe. When the bias potential exceeds the incident particle energy, the ions should no longer reach the probe. Biasing the probe would also facilitate independent measurement of the fluxes of ions and neutral atoms.

Another technique may involve exposure of two carbon films, one of which is covered by a thin layer of insulating material to shield the film from low energy particles. By comparing the response of the two carbon films, one with and one without the insulating layer, information about particle energies could be obtained.

Silicon has been found to be sufficiently insulating for this purpose. A silicon layer having a thickness of 200 Angstrom (20 nanometer) has been found to completely exclude hydrogen particles having an energy below about 500 eV, permitting penetration of substantially all such particles having an energy above about 1 keV. Likewise, a silicon layer having a thickness of 800 Angstrom (80 nanometer) has been found to effectively exclude particles having an energy below about 2 keV and permit penetration of substantially all particles having an energy above about 4 keV. This technique provides a way to detect low energy hydrogen doses as low as $10^{12}$ H/cm$^2$ in the presence of much larger amounts ($10^{15}$ to $10^{16}$ H/cm$^2$) of background hydrogen. This has been very difficult using previously available methods.

In probe studies of the plasma edge, it is believed that, in some cases, the incident particles have a distribution of energies and angles of incidence to the probe. To calculate the response of resistance probes in this case, TRIM was used to calculate the damage profiles for deuterium incident to a carbon film assuming a Maxwelian velocity distribution for the incident deuterium. These calculations show that the damage profiles can be closely approximated by an exponential:

$$\Gamma(x) = \frac{2kT\epsilon}{\lambda} e^{-X/\lambda} \quad (6)$$

with $\lambda = 0.0556$ (kT(eV))$^{0.926}$ nm, 50 eV < kT < 1000 eV, where kT is the Maxwellian temperature. Fro Maxwellian particles, the fraction of incident energy resulting in damage is $\epsilon = 0.35 \pm 0.03$ (assuming a displacement threshold of 5 eV) in the energy range 50 < kT < 200 eV, similar to the value for monoenergetic particles in the same energy range.

Figure 4:
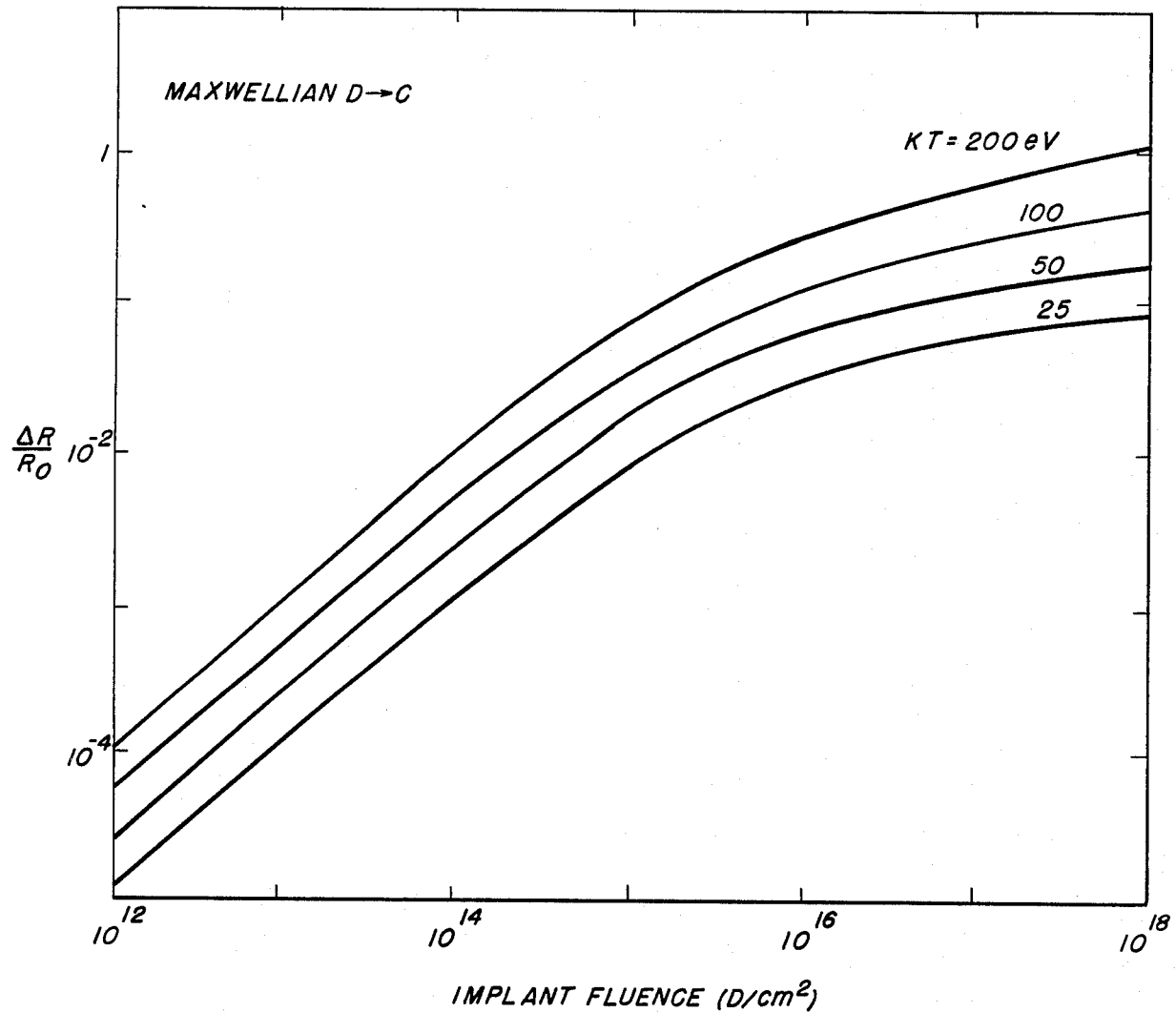
FIG. 4 graphically illustrates the calculated relative resistance changes for a carbon film implanted with deuterium for various Maxwellian temperatures.

FIG. 4 graphically illustrates calculated relative resistance changes for a carbon film having a thickness of 100 nm implanted with deuterium for various Maxwellian temperatures. The curves were calculated using Equations 4 and 6 with the same values for $\alpha$ and $\rho_o$ as for the monoenergetic case. In this case, the integral in Equation 4 can be solved analytically. For probe studies in which the incident particles can be assumed to have a Maxwellian velocity distribution, this model can be used to fit measurements of the fluence dependence of the resistance change, with energy and flux to be determined from the fit. Alternatively, probe biasing or insulated surface layers might be used to give energy discrimination, as described above.

The small size and relative ease of connecting current-inducing and voltage-measuring equipment to probes in accordance with the invention permits them to be used in positions which are difficult to access or where tritium contamination would complicate other methods of sample analysis. Probe resistance data can be continuously monitored during exposure of the probe to a plasma, a significant advantage over prior art devices and techniques.

While the invention has been described with reference to the accompanying drawings and particular embodiments, it is not limited to the details illustrated or described as various modifications may be made within the scope of the invention, the invention being limited only by the claims appended hereto.

I claim:

1. A probe for determining the energy and flux of particles in a plasma, comprising:
    a thin annealed carbon film adapted to be brought into contact with a plasma, said film having an electrical resistance which is related to the number of plasma particles impacting said film;
    means for passing an electrical current through said film; and
    means for determining the electrical resistance of said film to the current therethrough.

2. A probe as in claim 1, wherein said means for passing an electrical current through said carbon film comprises metal contacts in electrical contact with said film.

3. A probe as in claim 2, further comprising a substrate for supporting said contacts and said carbon film.

4. A probe as in claim 3, wherein said metal contacts comprise metal films deposited on said substrate, and said carbon film is deposited on said substrate in electrical contact with said metal films.

5. A probe as in claim 2, wherein said means for determining the electrical resistance of said carbon film comprises additional metal contacts in electrical contact with said carbon film.

6. A probe as in claim 5, comprising a substrate for supporting said metal contacts, said additional metal contacts and said carbon film, said metal contacts and said additional metal contacts comprising metal films deposited on said substrate and said carbon film is deposited on said substrate in electrical contact with said metal films.

7. A probe as in claim 5, comprising two of said metal contacts and two of said additional metal contacts;
    said carbon film comprising a portion thereof which is brought into contact with the plasma; and
    one of said metal contacts and one of said additional metal contacts is located on each side of said portion.

8. A probe as in claim 1, further comprising a thin insulating layer means for shielding said carbon film from low energy plasma particles.

9. A probe as in claim 8, wherein said carbon layer has a thickness of less than 100 nanometers, and said insulating layer means consists of a silicon layer having a thickness of 20 nanometers, whereby said insulating layer shields said film from hydrogen particles having an energy below about 500 eV.

10. A probe as in claim 8, wherein said carbon layer has a thickness of less than 100 nanometers, and said insulating layer means consists of a silicon layer having a thickness of 80 nanometers, whereby said insulating layer shields said film from hydrogen particles having an energy below about 2 keV.

11. A method for determining the energy or flux of particles in a plasma, comprising:
    exposing a carbon probe to said plasma, said probe having an electrical resistance which is related to the number of particles impacting said probe;
    passing an electrical current through said probe; and
    determining the electrical resistance of said probe to the current therethrough, whereby said energy and flux may be determined.

12. A method as in claim 11, further comprising shielding said probe from impact by particles having energy falling below a threshold.

13. A method as in claim 12, comprising shielding said probe by applying an insulating layer thereon.

14. A method as in claim 12, comprising shielding said probe by applying a positive bias voltage thereto.

15. A method as in claim 11, further comprising separating charged particles from neutral particles impacting said probe by applying a positive bias voltage to said probe.

* * * * *